(12) United States Patent
Rothstein et al.

(10) Patent No.: US 8,974,475 B2
(45) Date of Patent: Mar. 10, 2015

(54) METHODS AND DEVICES FOR CARDIAC VALVE REPAIR OR REPLACEMENT

(75) Inventors: Paul T. Rothstein, Elk River, MN (US); Jason Quill, Forest Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 781 days.

(21) Appl. No.: 12/771,011

(22) Filed: Apr. 30, 2010

(65) Prior Publication Data

US 2011/0270276 A1    Nov. 3, 2011

(51) Int. Cl.
| A61B 17/10 | (2006.01) |
| A61B 17/04 | (2006.01) |
| A61B 19/00 | (2006.01) |
| A61B 17/00 | (2006.01) |

(52) U.S. Cl.
CPC ............. *A61B 17/0401* (2013.01); *A61B 19/54* (2013.01); *A61B 2017/00243* (2013.01); *A61B 2017/00783* (2013.01); *A61B 2017/0409* (2013.01); *A61B 2017/0443* (2013.01); *A61B 2017/0464* (2013.01); *A61B 2017/0472* (2013.01)
USPC .......................................... 606/142

(58) Field of Classification Search
CPC .................. A61B 17/0401; A61B 2017/00243; A61B 2017/00867; A61B 2017/0409; A61B 2017/0464; A61B 2018/1407; A61B 17/221; A61B 17/064; A61B 17/068; A61F 2/2445; A61F 2230/0091; A61F 2/2451
USPC .......... 606/108, 113, 142, 143, 200; 623/2.36
See application file for complete search history.

(56) References Cited

U.S. PATENT DOCUMENTS

| 5,868,778 | A | 2/1999 | Gershony et al. |
| 6,558,349 | B1 * | 5/2003 | Kirkman .................. 604/104 |
| 6,595,989 | B1 | 7/2003 | Schaer |
| 6,629,534 | B1 | 10/2003 | St. Goar et al. |
| 7,191,015 | B2 | 3/2007 | Lamson et al. |
| 7,329,278 | B2 | 2/2008 | Seguin et al. |
| 7,381,219 | B2 | 6/2008 | Salahieh et al. |
| 7,731,681 | B2 | 6/2010 | Schaer et al. |
| 7,785,366 | B2 | 8/2010 | Maurer et al. |
| 7,881,807 | B2 | 2/2011 | Schaer |
| 2001/0034547 | A1 | 10/2001 | Hall et al. |

(Continued)

FOREIGN PATENT DOCUMENTS

| EP | 1834593 | 9/2007 |
| EP | 1852141 | 11/2007 |

(Continued)

OTHER PUBLICATIONS

Dictionary definition of "loop" from Merriam-Webster.*

*Primary Examiner* — Katherine M Shi (57) ABSTRACT

A delivery system for percutaneously guiding a repair or replacement device into a desired position relative to a valve within a patient. The delivery system includes a longitudinal support tube having a distal end, a deformable centering loop extending from the distal end of the support tube, at least one stop positioned on the centering loop and spaced from the distal end of the support tube, at least one clip delivery system slideably attached to the centering loop, and a sheath that is longitudinally slideable relative to the support tube, the centering loop, and the at least one clip delivery tube.

13 Claims, 10 Drawing Sheets

(56) References Cited

U.S. PATENT DOCUMENTS

| | | |
|---|---|---|
| 2005/0137700 A1 | 6/2005 | Spence et al. |
| 2006/0058871 A1* | 3/2006 | Zakay et al. .................. 623/2.18 |
| 2008/0045863 A1 | 2/2008 | Bakos |
| 2008/0177382 A1 | 7/2008 | Hyde et al. |
| 2008/0183194 A1 | 7/2008 | Goldfarb et al. |
| 2008/0255404 A1 | 10/2008 | Nogawa et al. |
| 2008/0288060 A1* | 11/2008 | Kaye et al. ................... 623/2.36 |
| 2009/0306685 A1* | 12/2009 | Fill ............................... 606/148 |

FOREIGN PATENT DOCUMENTS

| | | |
|---|---|---|
| WO | WO2006/002492 | 1/2006 |
| WO | WO2006/064490 | 6/2006 |
| WO | WO2009/061848 | 5/2009 |

\* cited by examiner

METHODS AND DEVICES FOR CARDIAC VALVE REPAIR OR REPLACEMENT

TECHNICAL FIELD

The present invention relates generally to devices and methods for repair of heart valves, and more particularly to devices and methods for use in repair and/or replacement of the mitral valve.

BACKGROUND

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with valves, which can generally be classified as either stenosis, in which a valve does not open properly, or insufficiency (also called regurgitation), in which a valve does not close properly. Stenosis and insufficiency may occur concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, and the ability of the heart to adapt to it, determine the treatment options that are available for a particular patient. In some cases, medication can be sufficient to treat the patient, which is the preferred option when it is viable; however, in many cases, defective valves have to be repaired or completely replaced in order for the patient to live a normal life.

One situation where repair of a mitral valve is often viable is when the defects present in the valve are associated with dilation of the valve annulus, which not only prevents competence of the valve but also results in distortion of the normal shape of the valve orifice. Remodeling of the annulus is central to these types of reconstructive procedures on the mitral valve. When a mitral valve is repaired, the result is generally a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position, which can restrict, remodel and/or support the annulus to correct and/or prevent valvular insufficiency. Such a repair technique can be referred to as a valve annuloplasty.

While such techniques can be effective for certain applications, these techniques typically apply to open heart surgery where the chest of the patient is opened, such as via a sternotomy, and then the patient is placed on cardiopulmonary bypass. Thus, open heart surgery can be relatively invasive and traumatic to the patient. In order to simplify surgical procedures and reduce patient trauma, there has been a recent increased interest in minimally invasive and percutaneous replacement and/or repair of cardiac valves. Replacement or repair of a heart valve in this way typically does not involve actual physical removal of the diseased or injured heart valve. Instead, in some cases, a replacement valve can be delivered in a compressed condition to a valve site, such as the pulmonary or aortic valve site, where it is expanded to its operational state. However, percutaneous replacement of a valve and/or minimally invasive valve repair in the area of the mitral valve has its own unique considerations due to the different physical characteristics and access limitations of the mitral valve as compared to the pulmonary and aortic valves. There is a continued desire to be able to be able to improve mitral valve repair and replacement devices and procedures to accommodate the physical structure of the heart without causing undue stress during surgery, such as providing devices and methods for repairing the mitral valve in a minimally invasive and/or percutaneous manner.

BRIEF DESCRIPTION OF THE DRAWINGS

The present invention will be further explained with reference to the appended Figures, wherein like structure is referred to by like numerals throughout the several views, and wherein.

SUMMARY

In accordance with the invention, devices and methods are provided for percutaneously guiding a transcatheter valve repair or replacement device into position relative to a valve that is to be repaired or replaced. In particular, sutures are percutaneously delivered and placed in certain predetermined positions relative to the native anatomy (e.g., to the patient's native mitral valve, tricuspid valve, or other anatomical structures), then a replacement valve or other device, such as a valve repair device, is moved along those sutures to the implantation or repair location. In one embodiment of the invention, attachment devices, such as u-clips, are percutaneously delivered using a delivery system and are subsequently or simultaneously attached to the anatomy of a patient, such as to the mitral valve annulus. In one particular embodiment, two u-clips or coiled clips are delivered and attached at predetermined locations in the mitral valve annulus, such as near the commissures. These clips can include extending sutures that are positioned inside the delivery system during the delivery process. Once these clips with their extending sutures are secured to the mitral valve annulus, the suture lines can be used to guide the mitral valve replacement or repair device to the correct location for implantation relative to the valve annulus. After the device is implanted, the clips and attached sutures can be removed from the patient, such as with a clip retrieval device that disengages the clips from the tissue of the patient.

In one particular embodiment of the invention, a delivery system is provided for percutaneously guiding a repair or replacement device into a desired position relative to a valve within a patient. The system generally includes a centering loop, at least two clip delivery tubes, and a sheath. The delivery system includes a longitudinal support tube having a distal end, a deformable centering loop extending from the distal end of the support tube, at least one stop positioned on the centering loop and spaced from the distal end of the support tube, at least one clip delivery system slideably attached to the centering loop, and a sheath that is longitudinally slideable relative to the support tube, the centering loop, and the at least one clip delivery tube. In accordance with the invention, a deformable clip with an extending suture can be provided in combination with the delivery system.

DETAILED DESCRIPTION

Figure 1:
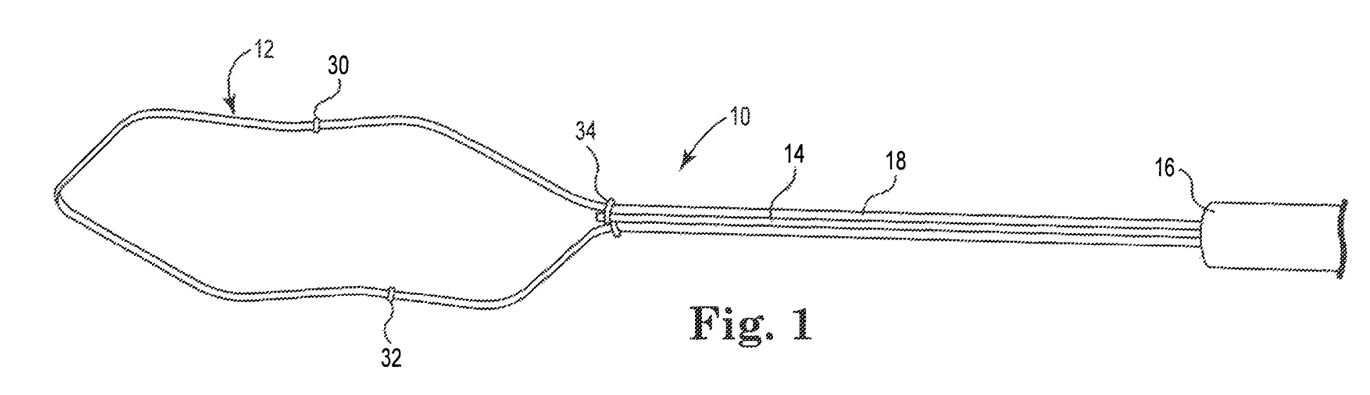
FIG. 1 is a front perspective view of a distal end of a delivery system of the invention for attaching suture devices to the anatomy of a patient and with its sheath in a first position.
Figure 2:
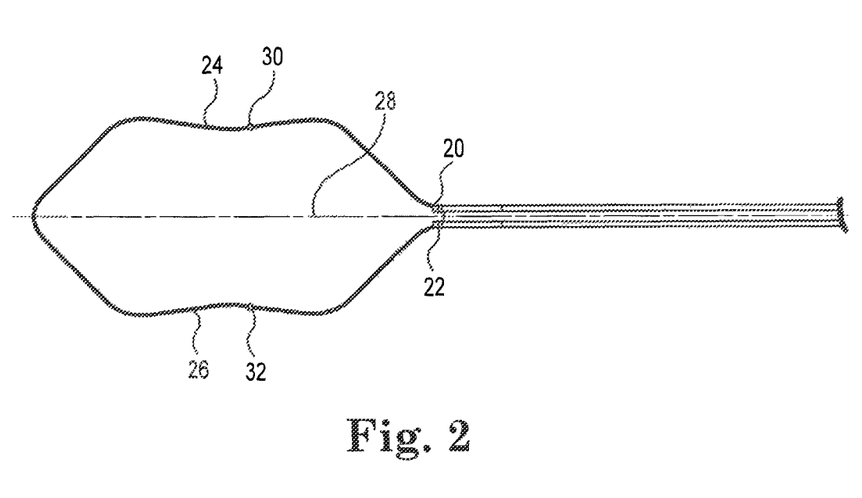
FIG. 2 is a front view of the portion of the delivery system illustrated in FIG. 1.
Figures 3, 4:
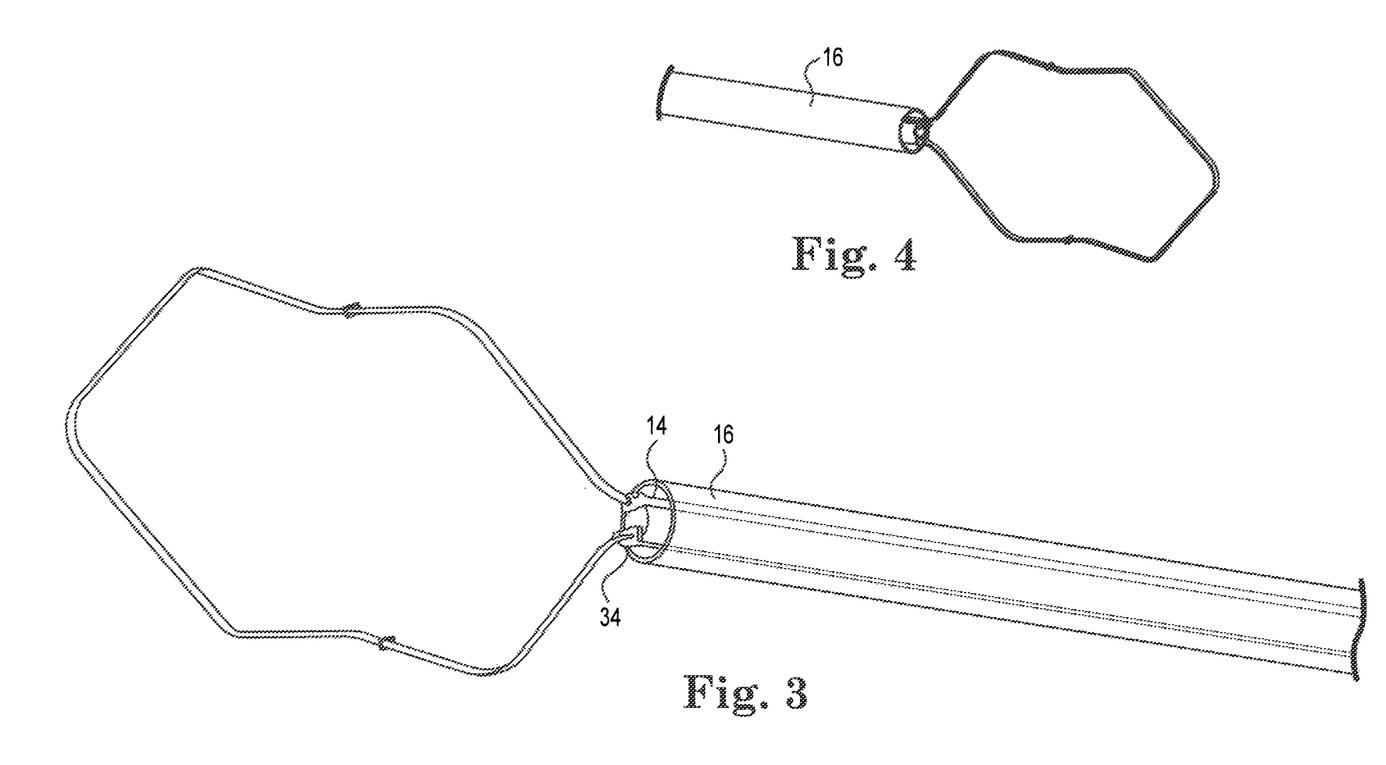
FIG. 3 is a perspective view of the portion of the delivery system illustrated in FIG. 1, with the sheath illustrated as transparent to better view the system components, and with the sheath in a second position relative to the distal end of the system.
FIG. 4 is another perspective view of the delivery system of FIG. 3, and illustrating the sheath as opaque.

Referring now to the Figures and initially to FIGS. 1-4, a distal end of a delivery system 10 is illustrated, which generally comprises a centering loop 12, at least one clip delivery tube 14, and a slideable sheath 16. The centering loop 12 includes two ends 20, 22, each of which extends from one end of a support tube 18. Support tube 18 extends longitudinally relative to the length of the delivery system 10. In FIG. 1, the sheath 16 is partially retracted relative to the clip delivery tubes 14, and in FIGS. 3 and 4, the sheath 16 is in a more distal position where it covers almost the entire length of the clip delivery tubes 14.

The centering loop 12 is made of a material that is generally compressible or deformable with the application of an external force, and self-expandable with removal of that external force, such as may be accomplished with a flat wire made of a shape memory material, such as Nitinol, stainless spring steel, or the like. The centering loop 12 of this embodiment includes a continuous piece of material comprising first and second portions 24, 26, and is generally configured as a modified "U" or "V" shape. First and second portions 24, 26 extend from the ends 20, 22, respectively, and meet at a distal end of the centering loop 12. The first and second portions 24, 26 can be mirror images of each other and can be symmetrical about a central axis 28 that generally extends through the support tube 18 and through the distal end of the centering loop 12. Alternatively, these first and second portions 24, 26 can be configured to be somewhat or substantially different from each other in such a way that the centering loop 12 does not have a line of symmetry. In yet another alternative, the first and second portions 24, 26 are separate pieces of material having the same or different material properties, which can be attached or bonded to each other and used to make up the structure of the centering loop 12.

In the illustrated embodiment, each of the first and second portions 24, 26 includes a first angled portion that extends from one of the ends 20, 22 and away from the central axis 28, a longitudinal portion that extends from the first angled portion toward the distal end of the centering loop 12, and a second angled portion that extends from the longitudinal portion toward the distal end of the centering loop 12 and toward the central axis. The second angled portions of the first and second portions 24, 26 meet at the distal end of the centering loop 12. This distal end of loop 12 is shown as having a relatively curved shape, although the end may instead include more of a sharp angle or be more curved or differently shaped than illustrated. The longitudinal portion of the first and second portions 24, 26 include a bow or curve toward the central axis of the centering loop 12, thereby providing a saddle or concave shape to the central area of the loop 12.

The centering loop 12 further includes two stops 30, 32, each of which is spaced from one of the ends 20, 22 on the first and second portions 24, 26, respectively. The stops 30, 32 may comprise separate clips or other structures that are attached to the wire structure of the centering loop 12, or may otherwise be formed to extend from the centering loop 12 in order to stop movement of a component of the delivery device along the wire structure, as discussed below. In one embodiment, the stops 30, 32 are positioned adjacent to the lowest point of the saddle shapes on the longitudinal portions of the first and second portions 24, 26, although it is contemplated that these stops 30, 32 can be located at any point along the lengths of the portions 24, 26. Both stops 30, 32 can be located at the same distance from their respective ends 20, 22, or can be located at different distances from these ends. Regardless of the embodiment, the centering device and stops are intended to function cooperatively. That is, centering device provides a mechanism to locate the mitral valve annulus and the stops direct the location in which the sutures and clips will be placed.

As described above, the delivery device 10 includes at least one clip delivery tube 14, and in this illustrated embodiment, the delivery device 10 includes two delivery tubes 14. These delivery tubes 14 are located generally on opposite sides of the support tube 18 from each other. Each of the delivery tubes 14 includes an attached link or linking member 34 that is positioned relatively close to its distal end, where each of the linking members 34 is attached both to a delivery tube 14 and to one of the first and second portions 24, 26 of the centering loop 12. In the configuration illustrated in FIGS. 1-4, these linking members 34 are positioned adjacent to the ends 20, 22 of the centering loop 12.

Figure 5:
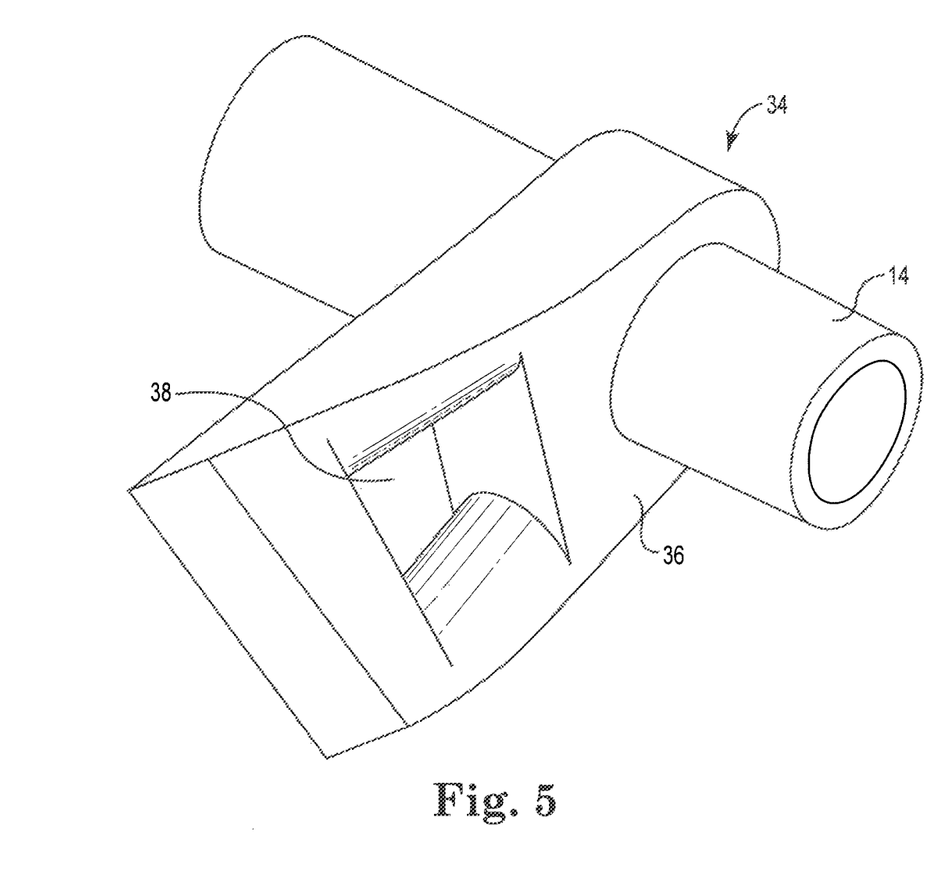
FIG. 5 is a perspective view of one embodiment of a linking member that is positionable adjacent to a distal end of a clip delivery tube of the invention.

One embodiment of a linking member 34 is illustrated in FIG. 5, and includes a body 36 with a first opening or aperture 38 that extends through it. Opening or aperture 38 is sized to allow the linking member 34 to slide along the centering loop 12 relatively easily, while maintaining a relatively secure attachment to the material of the centering loop 12. That is, the linking member 34 should be configured to allow it to move to a desired location along a portion of the centering loop 12 with a certain amount of force, while not substantially slipping or moving in any direction from this desired location unless a particular force is placed on the system components. Each linking member 34 is designed to allow the distal tip of a clip delivery tube 14 (a portion of which is shown in FIG. 5) to rotate in the same plane as the centering loop 12, and to allow the distal end of the clip delivery tube 14 to track along its respective portion 24, 26 of the centering loop 12 until it reaches one of its stops 30, 32. Thus, the opening 38 of each linking member 34 should be sized appropriately so that it cannot pass beyond the stops 30, 32. The linking member 34 can be made of a relatively flexible or semi-flexible material, although it is possible that it can incorporate a mechanical pivot, a larger opening 38, and/or some other configuration that allows the desired rotation of the clip delivery tube 14 relative to the centering loop 12.

Figure 6:
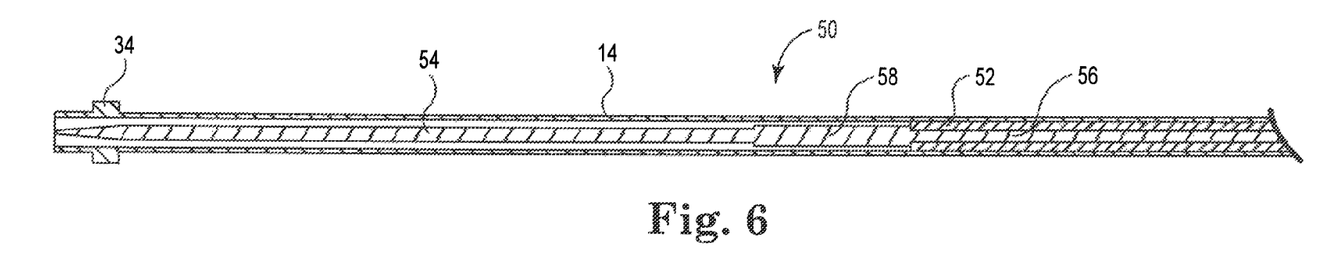
FIG. 6 is a cross-sectional view of a distal end of a clip delivery tube assembly.
Figure 9:
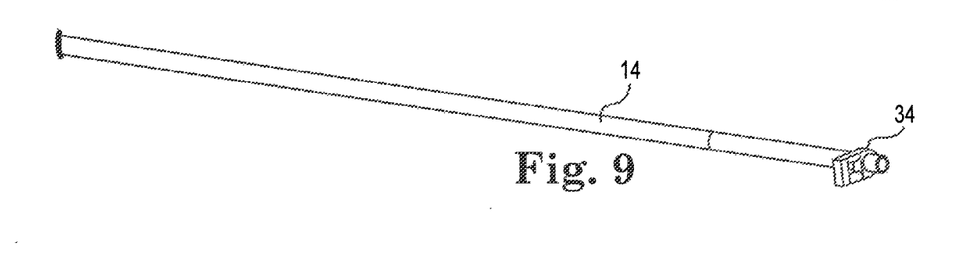
FIG. 9 is a perspective view of the clip delivery tube of FIG. 6 with a linking member adjacent to its distal end.

FIG. 6 is a cross-sectional view of one embodiment of a clip delivery system 50, which includes one of the clip delivery tubes 14 with a linking member 34 positioned at its distal end. A number of components are provided within the clip delivery tube 14, which are also illustrated separately in FIGS. 7-9 for a more clear view of one embodiment of these components. In particular, clip delivery system 50 includes the clip delivery tube 14 having a central opening in which a clip pusher 52 and a clip 54 are positioned. The clip 54 is attached to a suture 56 by a crimp sleeve 58 or other attachment method, device, or structure. The crimp sleeve 58 and suture 56 are also positioned within the central opening of the clip delivery tube 14. The crimp sleeve 58 is configured to cooperate with the clip pusher 52 for moving the clip 54 and attached suture from the clip delivery tube 14, as is explained further below. Therefore, if a different configuration or structure other than a crimp sleeve is used for attaching the suture 56 to the clip 54, another enlarged or extending structure may be included with the suture/clip combination in order to provide the ability for the clip pusher 52 to engage with the suture/clip combination to push the clip 54 from its distal end.

Figures 7, 8:
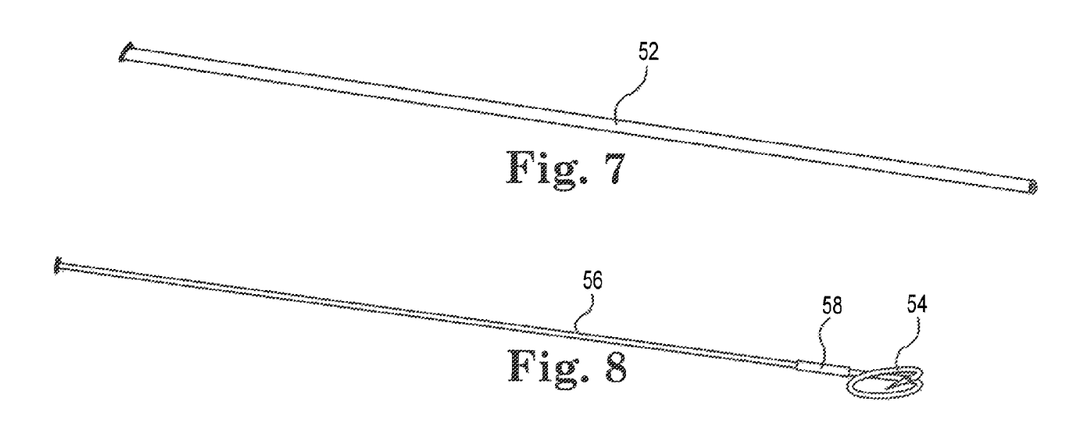
FIG. 7 is a perspective view of the clip pusher of FIG. 6.
FIG. 8 is a perspective view of the clip and extending suture of FIG. 6, with the clip in its coiled configuration.

Clip 54 is shown in its formed or relaxed condition in FIG. 8 and in its straightened condition in FIG. 6. Clip 54 can be made of a shape memory material, such as Nitinol, such that when it is not subjected to any external straightening forces, it will be coiled on itself in a manner similar to that shown in FIG. 8. However, when an external force is placed on the clip 54, such as can be provided by uncoiling the clip 54 and placing it within the central longitudinal opening of the clip delivery tube 14, it can be maintained in a relatively straight configuration by the walls of the opening of the clip delivery tube 14. The clip 54 can remain in this straightened configuration until any external forces are removed (e.g., the clip 54 is moved from the tube 14).

The clip pusher 52 is a tubular member with an internal opening though which the suture 56 can be passed. The clip pusher 52 is made of a relatively flexible material that also has enough structural integrity that it can be deformed as will be described below relative to the functioning of the delivery system 10. The crimp sleeve 58 acts as a shoulder for the clip pusher 52 so that the suture 56 and clip pusher 52 can be temporarily attached at the proximal end of the clip pusher and be used to draw the clip 54 into the clip delivery tube 14 and/or push the clip 54 out of the clip delivery tube 14. The distal tip or end portion of the clip delivery tube 14 may be made of a relatively rigid material such as stainless steel or a relatively rigid plastic, while the remainder of the clip delivery tube 14 may be made of a relatively flexible material. In particular, the portion of the clip delivery tube 14 that is made of a relatively rigid material can have a length that is at least as long as the straightened portion of the clip 54 that it will enclose, so that the rigid material can maintain the clip 54 in its straightened configuration.

Figure 10:
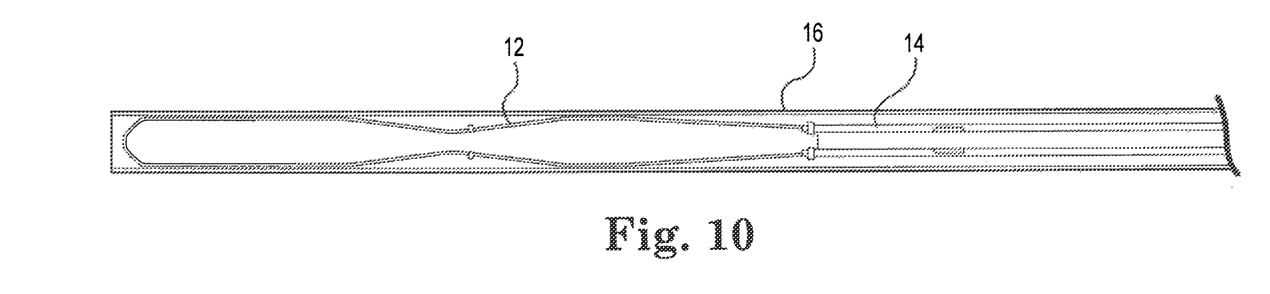
FIG. 10 is a front view of a distal end of a delivery system of the invention with its centering loop compressed and positioned within a sheath of the delivery system.

In order to deliver the centering loop 12 to a desired location within a patient, the centering loop 12 has to be collapsed or compressed so that it can be contained within the delivery system 10. In order to compress or collapse the centering loop 12, the sheath 16 is slid toward the distal end of the centering loop 12 until the entire length of the centering loop 12 is contained within the sheath 16, as is illustrated in FIG. 10. Optionally, the centering loop 12 can be grasped and compressed to allow the sheath 16 to slide more easily over the centering loop 12. In this embodiment, the entire assembly of the distal end of the device is attached at a proximal end to a handle (not shown). The handle may include a number of different mechanisms for controlling the delivery system components at the distal end of the system. One of these mechanisms can include a slider, button, or other component that is activated to move the sheath 16 toward the distal end of the centering loop 12. The handle may also include two additional mechanisms, such as sliders, buttons, or other components, which can be activated to move the clip delivery tubes 14 forward along the first and second portions 24, 26 of the centering loop 12 and toward their respective stops 30, 32. In addition, the device may include mechanisms, such as sliders, buttons, or the like, each of which can be activated to deploy one of the clips 54. The delivery system may be designed so that the mechanisms that move the clip delivery tubes 14 and the mechanisms that deploy the clips 54 act simultaneously or sequentially during the clip deployment process.

Figure 11:
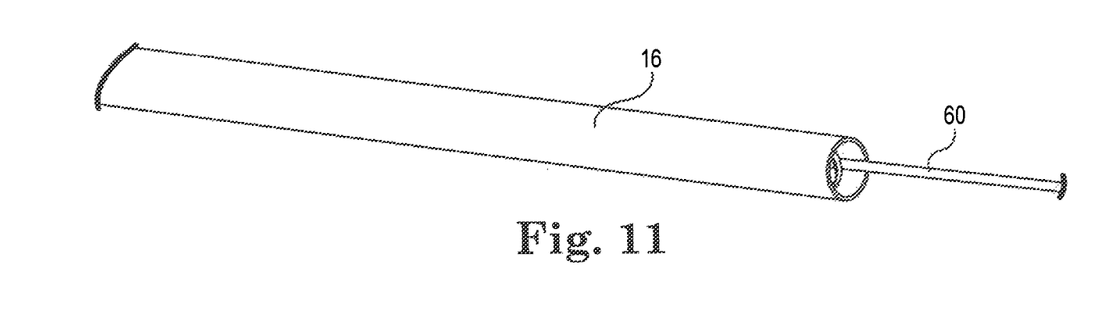
FIG. 11 is a perspective view of a distal end of a delivery system of the invention with an extending guidewire.
Figure 12:
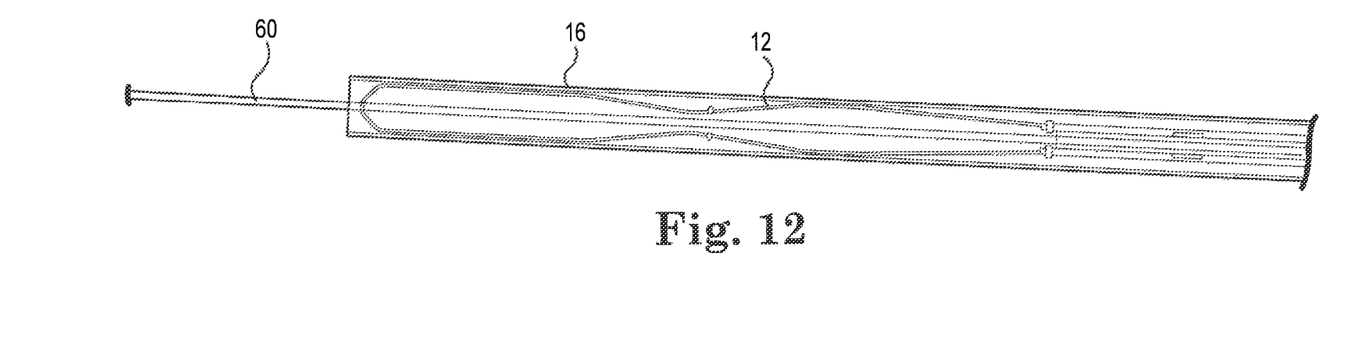
FIG. 12 is a front view of the distal end of the delivery system illustrated in FIG. 11.
Figure 13:
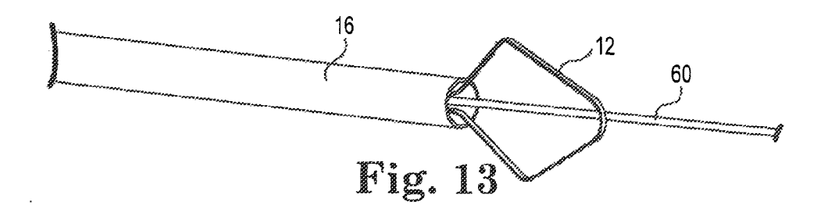
FIG. 13 is a perspective view of the distal end of the delivery system of FIGS. 11-12 with the centering loop partially deployed.
Figure 14:
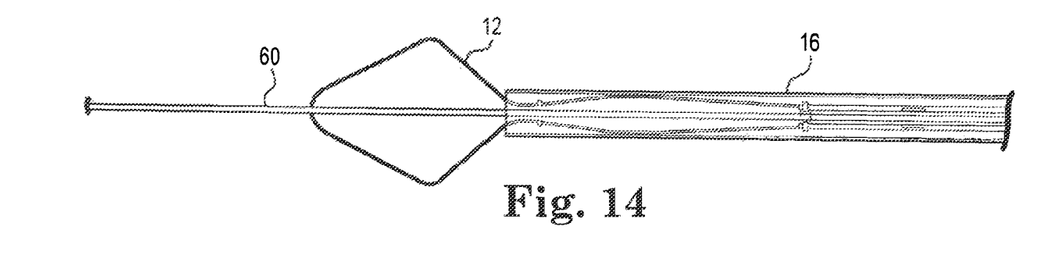
FIG. 14 is a front view of the distal end of the delivery system illustrated in FIG. 13.
Figure 15:
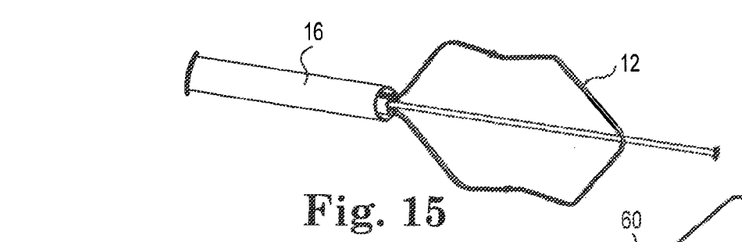
FIG. 15 is a perspective view of the distal end of the delivery system of FIGS. 10-14, with the centering loop fully deployed beyond the edge of a sheath of the delivery system.
Figure 16:
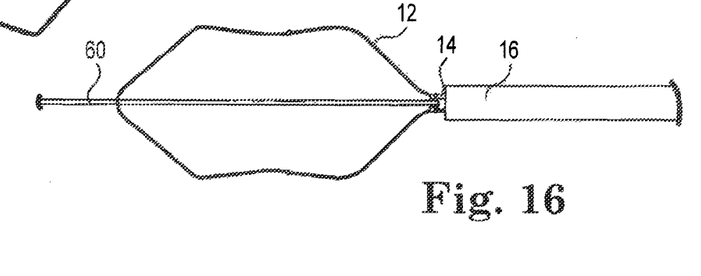
FIG. 16 is a front view of the distal end of the delivery system illustrated in FIG. 15.

In order to deploy the centering loop 12 within a location in a patient, such as for a mitral valve repair or replacement procedure, the delivery system 10 may further include a guidewire 60, as shown in FIG. 11, for example. The guidewire 60 can be advanced into and through the patient's left atrium, through the mitral valve annulus, and then into the left ventricle. The distal end of the delivery system 10, with its clips 54 loaded and fully sheathed, as is illustrated in FIGS. 11 and 12, can be inserted into the patient over the guidewire 60 and into the left ventricle. The sheath 16 can then be partially moved in a proximal direction relative to the centering loop 12 until the distal end of the centering loop 12 is partially released or deployed from the sheath 16, as is illustrated in FIGS. 13 and 14. Next, the sheath 16 can be moved further in a proximal direction relative to the centering loop 12 until the entire centering loop 12 is released or deployed from the sheath 16, as is illustrated in FIGS. 15 and 16. In this contiguration, the distal ends of the clip delivery tubes 14 can also be positioned outside the sheath 16. The operator can then guide the distal end of the delivery system 10 back from the left ventricle to position the centering loop 12 in a desired location. Alternatively, the centering loop 12 could be released or deployed in the left atrium and guided forward in the valve.

In one embodiment, the operator can pull the delivery system back from the left ventricle until the saddle or concave shaped area of the centering loop 12 is located at the commissures of the valve. A steerabie catheter may be required to assist in positioning of the centering loop 12. Additionally, steering may be incorporated into the sheath for this purpose. This process of locating the centering loop 12 relative to the patient's anatomy can be aided by the use of visualization techniques, such as fluoroscopy and the like. Further, once the device is at the area of the mitral valve annulus, the orientation or clocking of the centering loop 12 with respect to the mitral valve annulus can be determined. When the wires of the centering loop 12 are clocked correctly in the commissure-commissure direction of the mitral valve annulus, the anterior and posterior leaflets will still be able to coapt. However, if the wires of the centering loop 12 were instead positioned in the anterior-posterior direction of the mitral valve annulus, the wires would prevent the anterior and posterior leaflets from coapting during systole. In a clinical setting, clocking of the device can be accomplished with echocardiographic guidance using color flow Doppler, for example. The centering loop 12 can also be twisted until regurgitation is minimized, thereby ensuring proper device orientation.

Figure 17:
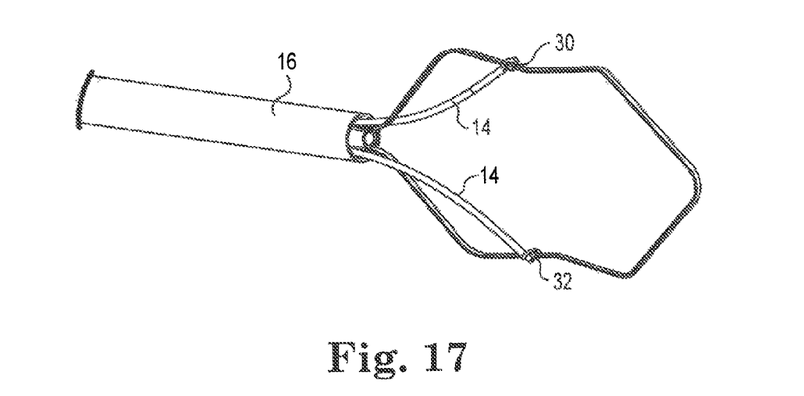
FIG. 17 is a perspective view of the distal end of the delivery system of FIGS. 15-16, with the centering loop deployed and the clip delivery tubes advanced to the stops of the centering loop.
Figure 18:
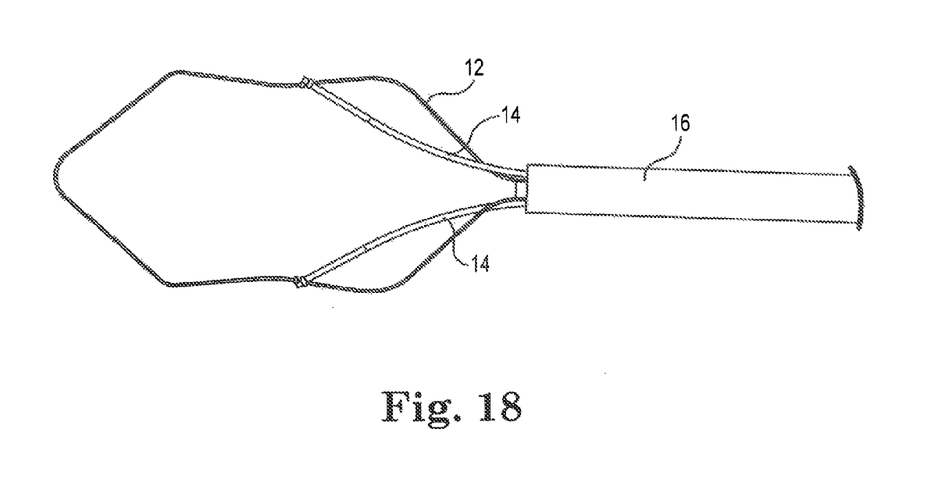
FIG. 18 is a front view of the delivery system illustrated in FIG. 17.
Figure 19:
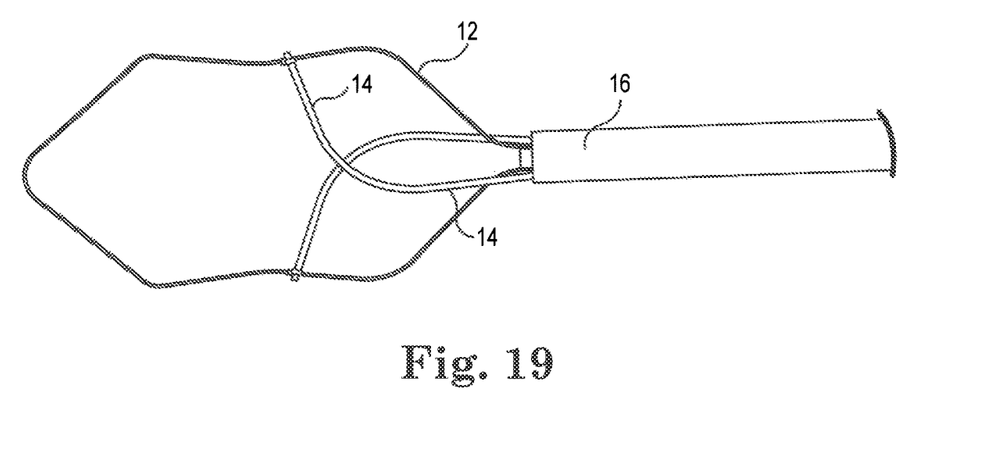
FIG. 19 is a front view of the distal end of the delivery system of FIGS. 17-18, with the clip delivery tubes further advanced from the sheath of the delivery system.
Figure 20:
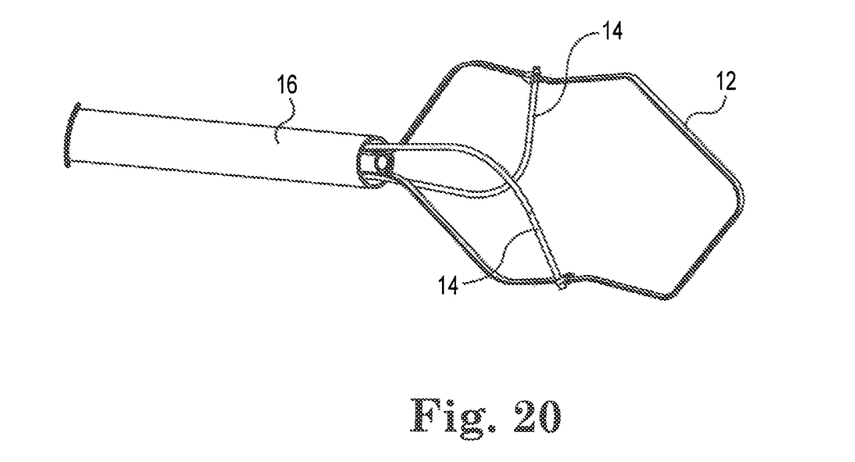
FIG. 20 is a perspective view of the delivery system illustrated in FIG. 19.

Once the centering loop 12 is correctly positioned relative to the mitral valve, the wires of the centering loop 12 are used to guide the delivery of the clip delivery tubes 14. First, the clip delivery tubes 14 are advanced distally so that the linking members slide along the wires of the centering loop 12, as is illustrated in FIGS. 17 and 18. When the clip delivery tubes 14 reach the stops 30, 32, the distal advancement of the clip delivery tubes 14 will stop, as is illustrated in FIGS. 17 and 18. The clip delivery tubes 14 can continue to be advanced distally, thereby deforming or bending the tubes 14, as is illustrated in FIGS. 19 and 20. As is illustrated in these Figures, the tubes 14 can be advanced until distal ends of the clip delivery tubes 14 are relatively perpendicular to the target tissue of the patient, thereby allowing for a better chance of tissue capture by the clips 54.

Figure 21:
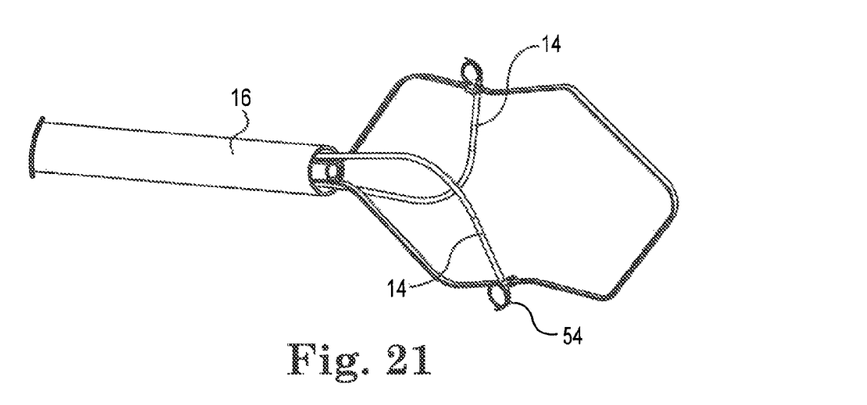
FIG. 21 is a perspective view of the delivery system of FIGS. 19-20, which shows the clips in their deployed configuration.
Figure 22:
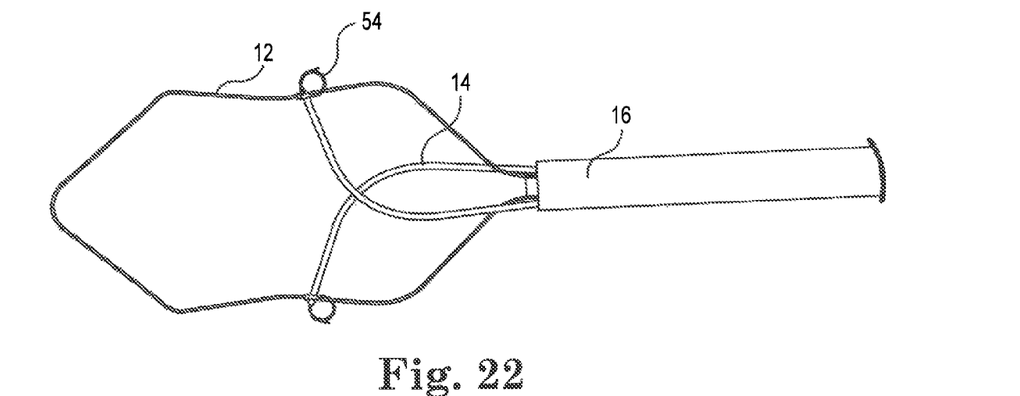
FIG. 22 is a front view of the delivery system illustrated in FIG. 21.

At this point, each of the clips 54 can be pushed from their clip delivery tubes 14 (e.g., with the clip pusher 52) until the sharp end of each clip 54 penetrates the tissue immediately adjacent to the distal end of the clip delivery tubes 14. With further advancement or movement of the clips 54 from the interior area of the clip delivery tubes 14, the shape memory material of the clips 54 will cause the clips to coil back toward their relaxed or coiled shape, thereby capturing the tissue. FIGS. 21 and 22 illustrate the situation where the clips 54 are deployed from the ends of the clip delivery tubes 14 and are in their relaxed or coiled configuration, which is the shape that these clips 54 will generally take when engaged with the heart tissue. If the deployment location of any of the clips is determined to be undesirable, it is possible to pull these clips 54 back into their respective clip delivery tubes 14, reorient the device, and then redeploy the clips 54.

Figure 23:
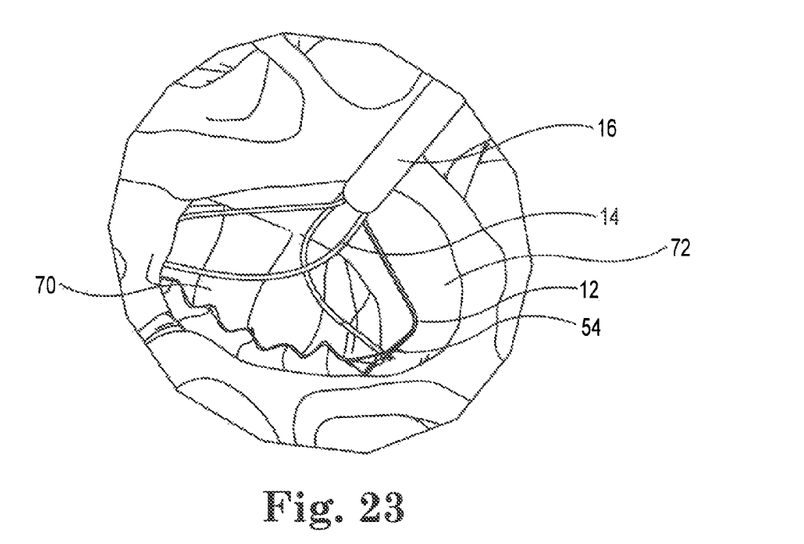
FIG. 23 is a perspective schematic view of a section of a heart in the area of a mitral valve, with the centering loop positioned relative to the mitral valve annulus and before the clips have been deployed.
Figure 24:
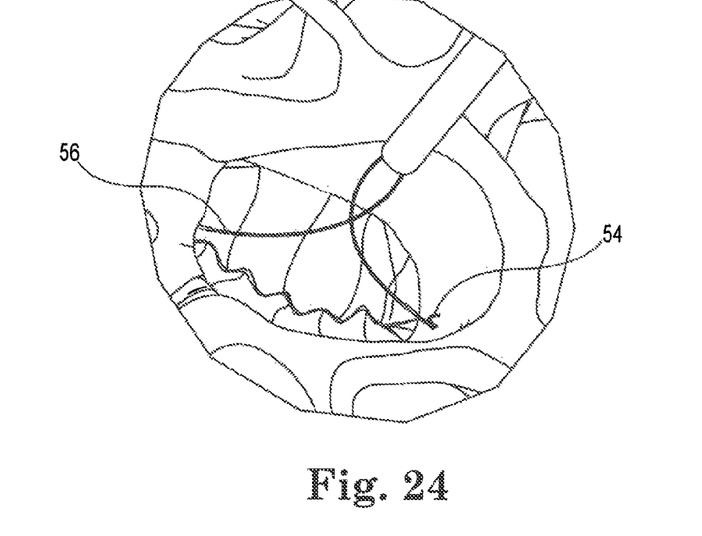
FIG. 24 is a perspective schematic view of a the section of the heart of FIG. 23, with the clips deployed and attached to tissue and with the clip delivery tubes retracted.

A schematic view of the delivery system 10 of the invention with the clips 54 deployed and positioned relative to a mitral valve space of a patient is illustrated in FIG. 23. In particular, the centering loop 12, clip delivery tubes 14, sheath 16, and deployed clips 54 are shown relative to a mitral valve 70 and left atrium 72. Once the clips 54 are deployed, centering loop 12, clip delivery tubes 14, and sheath 16 can be removed from the area of the mitral valve, which will leave the guidewire and clips 54 with extending suture material 56 in place within the patient, as is illustrated in FIG. 24.

The sutures and guidewire can then be used with a mitral valve repair or replacement device to complete the surgical procedure, where a number of different devices and procedures may be utilized. In general, a delivery system of a mitral valve repair or replacement device can follow either the guidewire, one of the suture lines, or both, depending on the application. In the case of a transcatheter valve, the delivery system could follow along the guidewire, with the suture lines looped from the outside of its frame to the inside of its frame. When the valve is deployed, the location of the looped suture on the frame could align with the clip. Alternatively, in the case of a percutaneous repair device, the suture lines may be used as guides to the annulus, without the use of the guidewire.

After the implantation and removal of the repair or replacement device, the clips can also be removed from the patient. One exemplary device that could aid in this removal of clips is a small braided catheter with a metal section at the distal end that can follow over the suture line. Once it reaches the area of the clips, tension can be applied, thereby drawing the clip into the metal section of the catheter, thereby disengaging it from the tissue of the patient.

Although the delivery systems of the invention are described herein with regard to methods for repairing or replacing the mitral valve, it is understood that the delivery systems can also be used for other areas of the heart (e.g., for repair or replacement of the tricuspid valve), or in the area of other anatomical structures of the body. It is further understood that the repair or replacement devices that can be guided along the delivered sutures can include annuloplasty devices, pharmaceutical, biological, or other therapies, or other percutaneously deliverable devices, for example.

The present invention has now been described with reference to at least one embodiment thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A delivery system for percutaneously delivering and attaching at least one clip and attached suture in a desired position within a patient, the delivery system comprising:
   a longitudinal support tube having a distal end;
   a deformable centering loop extending from the distal end of the support tube, the centering loop having a length, an exterior surface, a first portion and a second portion, wherein the first portion and the second portion meet at a distal end of the centering loop;
   at least one stop positioned on the centering loop and spaced from the distal end of the support tube;
   at least one clip delivery system slidably attached to the centering loop, wherein the at least one clip delivery system is slidable over the exterior surface of the centering loop until it reaches the at least one stop positioned thereon; and a sheath that is longitudinally slidable relative to the support tube, the centering loop, and the at least one clip delivery system.

2. The delivery system of claim 1, wherein the centering loop comprises a shape memory material.

3. The delivery system of claim 1, wherein each clip delivery system comprises a clip delivery tube having a central opening.

4. The delivery system of claim 3, in combination with at least one clip and a suture extending from the clip, wherein each clip and suture is positionable within the central opening of the clip delivery tube.

5. The delivery system of claim 4, wherein at least one of the clips comprises a shape memory material.

6. The delivery system of claim 4, wherein at least one of the clips comprises a coiled shape.

7. The delivery system of claim 4, wherein at least one of the clips comprises a tissue-piercing distal end.

8. The delivery system of claim 4, further comprising a clip pusher slideably positioned within the central opening of the clip delivery tube.

9. The delivery system of claim 8, further comprising a shoulder portion located between each clip and suture, wherein the shoulder portion is engageable with a distal end of the clip pusher.

10. The delivery system of claim 9, wherein the shoulder portion comprises a crimp sleeve.

11. The delivery system of claim 1, wherein the first portion and the second portion of the centering loop are a unitary structure.

12. A delivery system, for percutaneously delivering and attaching at least one clip and attached suture in a desired position within a patient, the delivery system comprising:

a longitudinal support tube having a distal end;

a deformable centering loop extending from the distal end of the support tube, the centering loop having a length, an exterior surface, a first portion and a second portion, wherein the first portion and the second portion meet at a distal end of the centering loop;

at least one stop positioned on the centering loop and spaced from the distal end of the support tube;

at least one clip delivery system slidably attached to the centering loop, wherein each clip delivery system comprises a clip delivery tube comprising a distal end and a linking member attached to the clip delivery tube adjacent to its distal end, wherein the linking member is slidable along the length of the exterior surface of the centering loop; and a sheath that is longitudinally slidable relative to the support tube, the centering loop, and the at least one clip delivery system.

13. The delivery system of claim 12, wherein each linking member is slidable along the length of the exterior surface of the centering loop from the distal end of the support tube to one of the stops.

* * * * *